United States Patent [19]

Steffens

[11] 4,377,408
[45] Mar. 22, 1983

[54] HERBICIDAL DERIVATIVES OF 5-PHENOXY-4(3H)-QUINAZOLINONE-1-OXIDE

[75] Inventor: James J. Steffens, Yardley, Pa.

[73] Assignee: Rhone-Poulenc Agrochimie, Lyons, France

[21] Appl. No.: 286,747

[22] Filed: Jul. 27, 1981

[51] Int. Cl.³ ............... A01N 21/00; C07D 239/90
[52] U.S. Cl. .................... 71/92; 544/279; 544/284; 544/287; 544/289; 544/290
[58] Field of Search ............... 544/284, 287, 289, 290; 71/92

[56] References Cited

U.S. PATENT DOCUMENTS

| | | | |
|---|---|---|---|
| 3,476,756 | 11/1969 | Taylor et al. | 544/284 |
| 3,481,928 | 12/1969 | Wolf et al. | 544/289 |
| 3,784,635 | 1/1974 | Theissen | 71/98 |
| 3,907,866 | 9/1975 | Theissen | 71/111 |
| 3,983,168 | 9/1976 | Theissen | 71/107 |
| 4,063,929 | 12/1977 | Bayer et al. | 71/115 |
| 4,209,318 | 6/1980 | Johnson | 71/88 |
| 4,285,723 | 8/1981 | Cartwright et al. | 71/103 |

Primary Examiner—Donald G. Daus
Assistant Examiner—James H. Turnipseed
Attorney, Agent, or Firm—Morgan, Finnegan, Pine, Foley & Lee

[57] ABSTRACT

Herbicidal derivatives of 5-phenoxy-4(3H)-quinazolinone-1-oxide of the formula:

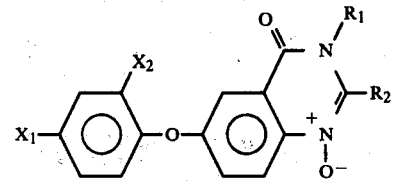

wherein $X_1$ is trihalomethyl; $X_2$ is halo; $R_1$ is H or ($C_1$–$C_5$) alkyl, which may be unsubstituted or substituted with hydroxy, alkoxy, cyano, halo or COO alkyl; and $R_2$ is H.

5 Claims, No Drawings

HERBICIDAL DERIVATIVES OF 5-PHENOXY-4(3H)-QUINAZOLINONE-1-OXIDE

BACKGROUND OF THE INVENTION

Herbicidal 5-[2-chloro-4-(trifluoromethyl)phenoxy]-2-nitrobenzoic acid and salts thereof, and various herbicidal derivatives of these compounds have been proposed including alkyl and cycloalkyl esters, alkylthio esters, phenyl ester, alkyl and dialkyl amido and benzoyl chloride forms. U.S. Patents which describe such compounds and the like include U.S. Pat. Nos. 3,652,645; 3,784,635; 3,873,302; 3,983,168; 3,907,866; 3,798,276; 3,928,416; and 4,063,929.

SUMMARY OF THE INVENTION

This invention provides certain herbicidal compounds of the formula:

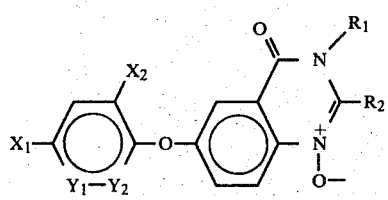

where:
(i) $Y_1$ is C-H or N;
(ii) $Y_2$ is $C-X_3$ or N, provided that $Y_1$ is not N when $Y_2$ is $C-X_3$; and
(iii) $X_1$, $X_2$, $X_3$, $R_1$ and $R_2$ are groups which are capable of being incorporated into formula I and which collectively impart herbicidal activity thereto.

Examples of the groups $X_1$, $X_2$, $X_3$, $R_1$ and $R_2$ are as follows:

$X_1$ and $X_2$ may be the same or different and may be selected from the group consisting of halo (e.g., Cl, Br and F), cyano, nitro and trihalomethyl(e.g., $CF_3$);

$X_3$ may be H or any of the groups exemplified above for $X_1$ and $X_2$;

$R_1$ and $R_2$ may be the same or different and may be hydrogen or a hydrocarbyl group (substituted or unsubstituted, e.g., having from 1 to 12 carbon atoms).

More particular examples of the $R_1$ hydrocarbyl groups include $C_1-C_5$ alkyl, alkenyl, aryl, aralkyl all of which may be optionally substituted with hydroxyl, alkoxy, cyano, halo (e.g., cl, Br and F) or COO alkyl. More particular examples of $R_2$ include $C_1-C_3$ alkyl and trifluoromethyl.

A preferred form of compounds of formula I is represented by the formula

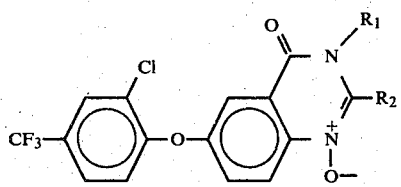

The following compound was prepared:

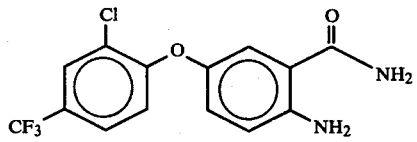

5-(2-chloro-4-trifluoromethylphenoxy)-2-nitrobenzamide (7.2 gm, 0.02 mole) was added to a stirred solution of $SnCl_2 2H_2O$ (10.3 gm, 0.066 mole) in glacial acetic acid (100 ml) saturated with HCl gas. After 3 hours the reaction mixture was poured on crushed ice (300 gm). The precipitated product was filtered, washed with water, and crystallized from acetonitrile. 2.07 gm of product was obtained having m.p. 195°–198°.

II and III may be prepared similarly

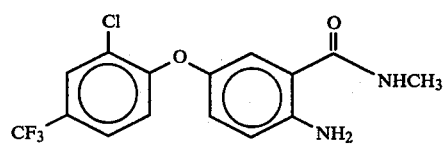

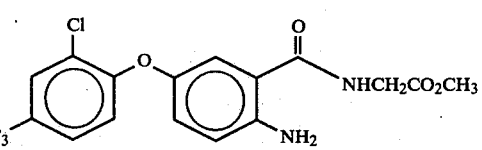

Preparation of IV

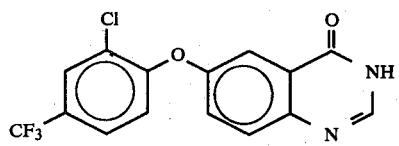

Compound I (2.0 gm) was refluxed in triethyl orthoformate for 1 hour. The resulting clear solution was cooled to −5° overnight. The crystalline solid which separated was filtered and washed with ether. Yield 1.0 gm of material having m.p]. 178.5°–180°.

IR(KBr) 3420, 3170, 3020, 2900, 1670, 1610, 1480 $cm^{-1}$.

Compounds V and VI are prepared similarly

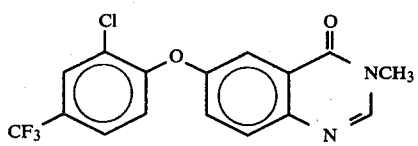

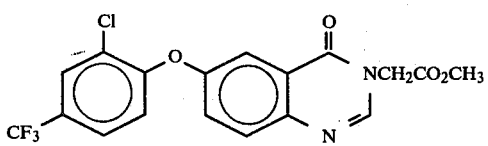

Compounds VII–IX may be prepared from the corresponding quinoxalinones by reaction with a 10% excess of 30% $H_2O_2$ in trifluoroacetic acid at 50°. The products are obtained by evaporation of solvent and crystallization from a suitable solvent.

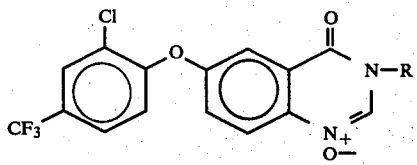

VII: R=H
VIII: R=CH₃
IX: R=CH₂CO₂CH₃

The compounds of this invention can be applied in various ways to achieve herbicidal action. They can be applied per se, but may be applied as the toxic components in pesticidal compositions of the compound and a carrier. These compositions may be applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil. In practice, herbicidal application is measured in terms of pounds of herbicide applied per acre. The compounds of this invention are effective herbicides when applied in herbicidal amounts, e.g., at rates between about 0.03 pound and about 10 pounds per acre.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A herbicidal compound of the formula

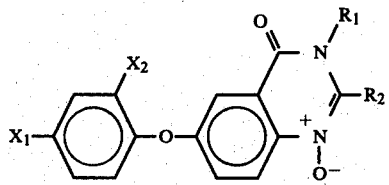

wherein $X_1$ is trihalomethyl; $X_2$ is halo; $R_1$ is hydrogen or $(C_1-C_5)$ alkyl, which may be unsubstituted or substituted with hydroxy, $(C_2-C_3)$ alkoxy, cyano, halo or $(C_1-C_3)$ COO alkyl; and $R_2$ is hydrogen.

2. A herbicidal compound according to claim 1 of the formula

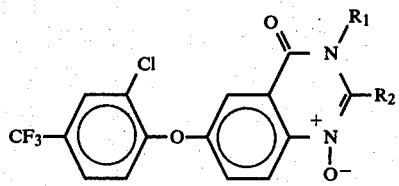

wherein $R_1$ is hydrogen or $(C_1-C_5)$ alkyl, which may be unsubstituted or substituted with $(C_2-C_3)$ COO alkyl, and $R_2$ is hydrogen.

3. A compound according to claim 1 of the formula

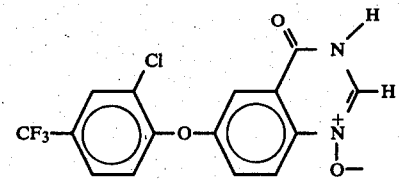

4. A herbicidal composition comprising a herbicidally effective amount of a compound according to claim 1 and an agronomically acceptable carrier.

5. A method for combating unwanted plants which comprises contacting them with a herbicidally effective amount of a compound according to claim 1.

* * * * *

UNITED STATES PATENT AND TRADEMARK OFFICE
CERTIFICATE OF CORRECTION

PATENT NO. : 4,377,408
DATED : Mar. 22, 1983
INVENTOR(S) : James J. Steffens

It is certified that error appears in the above-identified patent and that said Letters Patent is hereby corrected as shown below:

Claim 1, column 4, line 13, "$(C_2-C_3)$" should read -- $(C_1-C_3)$ --.

Claim 2, column 4, line 28, "$(C_2-C_3)$" should read -- $(C_1-C_3)$ --.

Signed and Sealed this

Twenty-fourth Day of May 1983

[SEAL]

Attest:

DONALD J. QUIGG

Attesting Officer

Acting Commissioner of Patents and Trademarks